US008930225B2

(12) United States Patent
Morris

(10) Patent No.: US 8,930,225 B2
(45) Date of Patent: *Jan. 6, 2015

(54) ESTIMATING HEALTHCARE OUTCOMES FOR INDIVIDUALS

(75) Inventor: MacDonald Morris, Atherton, CA (US)

(73) Assignee: Evidera Archimedes, Inc., San Francisco, CA (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/448,055

(22) Filed: Apr. 16, 2012

(65) Prior Publication Data

US 2012/0245953 A1    Sep. 27, 2012

Related U.S. Application Data

(63) Continuation of application No. 12/146,727, filed on Jun. 26, 2008, now Pat. No. 8,224,665.

(51) Int. Cl.
| | |
|---|---|
| G06Q 50/22 | (2012.01) |
| G06Q 50/24 | (2012.01) |
| G06F 19/00 | (2011.01) |
| G06Q 10/10 | (2012.01) |
| G06Q 40/08 | (2012.01) |

(52) U.S. Cl.
CPC .............. *G06Q 40/08* (2013.01); *G06Q 50/24* (2013.01); *G06F 19/328* (2013.01); *G06Q 10/10* (2013.01); *G06F 19/3437* (2013.01); *G06Q 50/22* (2013.01); *G06F 19/325* (2013.01)
USPC ........................................................... 705/3

(58) Field of Classification Search
CPC ........... G06Q 50/22; G06Q 50/24; A61B 5/01
USPC ......................................... 705/2, 3; 600/300
See application file for complete search history.

(56) References Cited

U.S. PATENT DOCUMENTS 6,108,635 A * 8/2000 Herren et al. ..................... 705/2
7,136,787 B2 11/2006 Schlessinger et al.

(Continued)

FOREIGN PATENT DOCUMENTS

EP             0917178         5/1999
WO     WO 2005/117553    12/2005

OTHER PUBLICATIONS

"Clinical Outcomes and Cost-Effectiveness of Strategies for Managing People at High Risk for Diabetes" (Eddy, David M. et al., American College of Physicians, Aug. 2005, 30 pgs).*

(Continued)

*Primary Examiner* — Michelle L Le
(74) *Attorney, Agent, or Firm* — Hickman Palermo Truong Becker Bingham Wong LLP

(57) ABSTRACT

A method and apparatus for predicting a health benefit for an individual is provided. Outcomes from a first simulation on a set of simulated individuals reflecting a population are stored and used to determine a first risk function and corresponding cost values. Outcomes from a second simulation on a set of simulated individuals reflecting having a healthcare intervention are stored and used to determine a second risk function reflecting the intervention and corresponding cost values of the intervention. A benefit function is derived from the difference of the first and second risk functions. A cost function that describes the cost of the intervention is derived from the respective cost values. The derived benefit function and cost function are used to predict the corresponding benefit and cost of the healthcare intervention for a given individual. Individuals can be ranked by degree of expected benefit.

20 Claims, 8 Drawing Sheets

(56) References Cited

U.S. PATENT DOCUMENTS

| | | |
|---|---|---|
| 2003/0065535 A1 | 4/2003 | Karlov et al. |
| 2004/0243441 A1 | 12/2004 | Bocionek et al. |
| 2005/0119534 A1 | 6/2005 | Trost et al. |
| 2005/0125158 A1 | 6/2005 | Schlessinger et al. |
| 2006/0129427 A1* | 6/2006 | Wennberg ............ 705/2 |
| 2006/0129428 A1 | 6/2006 | Wennberg |
| 2006/0173663 A1 | 8/2006 | Langheier |
| 2006/0292535 A1 | 12/2006 | O'Connor et al. |
| 2007/0038475 A1 | 2/2007 | Schlessinger et al. |
| 2008/0015894 A1 | 1/2008 | Miller et al. |
| 2009/0144082 A1 | 6/2009 | Selbst et al. |
| 2010/0198571 A1 | 8/2010 | Morris et al. |
| 2010/0305964 A1 | 12/2010 | Eddy et al. |

OTHER PUBLICATIONS

Schlessinger, Leonard, et al., "Archimedes: A new model simulating health care systems—the mathematical formulation", Academic Press, Journal of Biomedical Informatics, Nov. 2001, 14 pages.

Eddy, David M. et al., "Archimedes a trial-validated model of diabetes", Original Article, Emerging Treatments and Technologies, Nov. 2003, 9 pages.

Eddy, David M. et al., "Clinical Outcomes and Cost-Effectiveness of Strategies for Managing People at High Risk for Diabetes", American College of Physicians.

Notification of Transmittal of the International Search Report and the Written Opinion of the International Searching Authority, or the Declaration received in PCT Application No. PCT/US09/62005 dated Jun. 14, 2010 (11 pages).

Current Claims for PCT Application No. PCT/US09/62005, Jul. 2010 (7 pages).

Bajdik, C. et al., "A computer model to simulate family history of breast/ovarian cancer in BRCA1 mutation carriers" dated Aug. 23, 1999 (13 pages).

Dinh, T. et al., "Health Benefits and Cost Effectiveness of Primary Genetic Screening for Lynch Syndrome in the General Population" dated Jan. 2011 (14 pages).

Sibert, A. et al., "The effect of disease penetrance, family size, and age of onset on family history with application to setting eligibility criteria for genetic testing" dated Jan. 8, 2003 (8 pages).

Singh, D. et al., "Gene expression correlates of clinical prostate cancer behavior" *Cancer Cell* Mar. 2002 (pp. 203-209).

Stephenson, R. et al., "Flow Cytometry of Prostate Cancer: Relationship of DNA Content to Survival" *American Association for Cancer Research* May 1, 1987 (pp. 2504-2507).

"Notification of Transmittal of the International Search Report and the Written Opinion of the International Searching Authority, or the Declaration" received in international application No. PCT/US09/48803 dated Feb. 16, 2010 (11 pages).

Current claims of international application No. PCT/US09/48803, Mar. 2010 (4 pages).

Eddy, David M. et al., "Validation of the Archimedes Diabetes Model", Emerging Treatment and Technologies, Original Article, Nov. 2003, 9 pages.

\* cited by examiner

ESTIMATING HEALTHCARE OUTCOMES FOR INDIVIDUALS

CROSS-REFERENCE TO RELATED APPLICATIONS; BENEFIT CLAIM

This application claims the benefit under 35 U.S.C. §120 as a Continuation of application of Ser. No. 12/146,727, filed Jun. 26, 2008, now U.S. Pat. No. 8,224,665 the entire contents of which is hereby incorporated by reference as if fully set forth herein. The applicant hereby rescinds any disclaimer of claim scope in the parent application or the prosecution history thereof and advises the USPTO that the claims in this application may be broader than any claim in the parent application.

TECHNICAL FIELD

The present disclosure generally relates to using computers for estimating health outcomes for health interventions associated with individuals.

BACKGROUND

Rapid increases in the cost of healthcare are creating a growing demand for ways to reduce costs while minimizing the impact on healthcare quality and maintaining a high standard of care. HMOs, higher co-pays, tiered co-pays, formulary control, step therapy, disease management, predictive modeling, high-deductible plans, wellness plans, negotiated rates, referral requirements, centers of excellence, pre-authorization, offshore surgery options, wellness programs, and various educational and preventive programs are all initiatives driven by this goal.

The search for approaches that save money by improving care in cost-effective ways has led to screening and prevention measures such as blood pressure control, lipid-lowering therapy, weight reduction, aspirin, and cancer screening. These approaches are of particular interest because they offer the promise of improving patient health while reducing costs by averting more expensive outcomes. Some preventive interventions, such as prescribing beta-blockers after a heart attack, have been shown to be cost-effective on a short-term basis. Other preventive interventions are not as clear, or because they take longer to achieve cost-effectiveness, have been more difficult to assess.

Researchers have investigated the cost-effectiveness of various preventive interventions. Such work focuses on the cost-effectiveness of applying medical guidelines that specify the populations to whom the interventions should be applied. Example applied medical guidelines include simple rules incorporating a few factors that a doctor might be able to remember.

Medical risk calculators assess only the risk of a health outcome. Risk calculators are primarily used for selecting populations for treatment. Furthermore, risk calculators are generally derived from statistical analysis of a longitudinal data set and have a number of associated limitations. For example, in a purely statistical model, the size of the dataset limits the number of variables that can be fitted reasonably. Statistical analyses cannot model new interventions for which there is no data. As well, statistical analyses cannot model combinations of interventions which haven't been tested and for which there is no data. As well, statistical analyses cannot predict changes in a population for which there is no data. As well, statistical models cannot distinguish causal differences from behavioral associations; for example a statistical model may conclude that going to the doctor makes people sick, or getting chemotherapy causes you to die of cancer. Simulation models can be constructed using evidence from many different randomized controlled trials in which the true effect of each intervention or treatment is not confounded by behavioral biases.

Some approaches for identifying members of a payer who are at risk of a medical event or qualify for an intervention include analysis of claims data, analysis of health risk assessment (HRA) data, and predictive modeling. Some approaches for managing interventions in a cost-effective manner include disease management, adherence to guidelines, and wellness programs. Identification based on claims data generally is performed only after disease diagnosis and thus may have a limited utility, e.g., an intervention opportunity may be missed. Guidelines may be "one size fits all" instruments and the interventions specified in the guidelines may not be optimally targeted.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

DETAILED DESCRIPTION

Figure 1A:
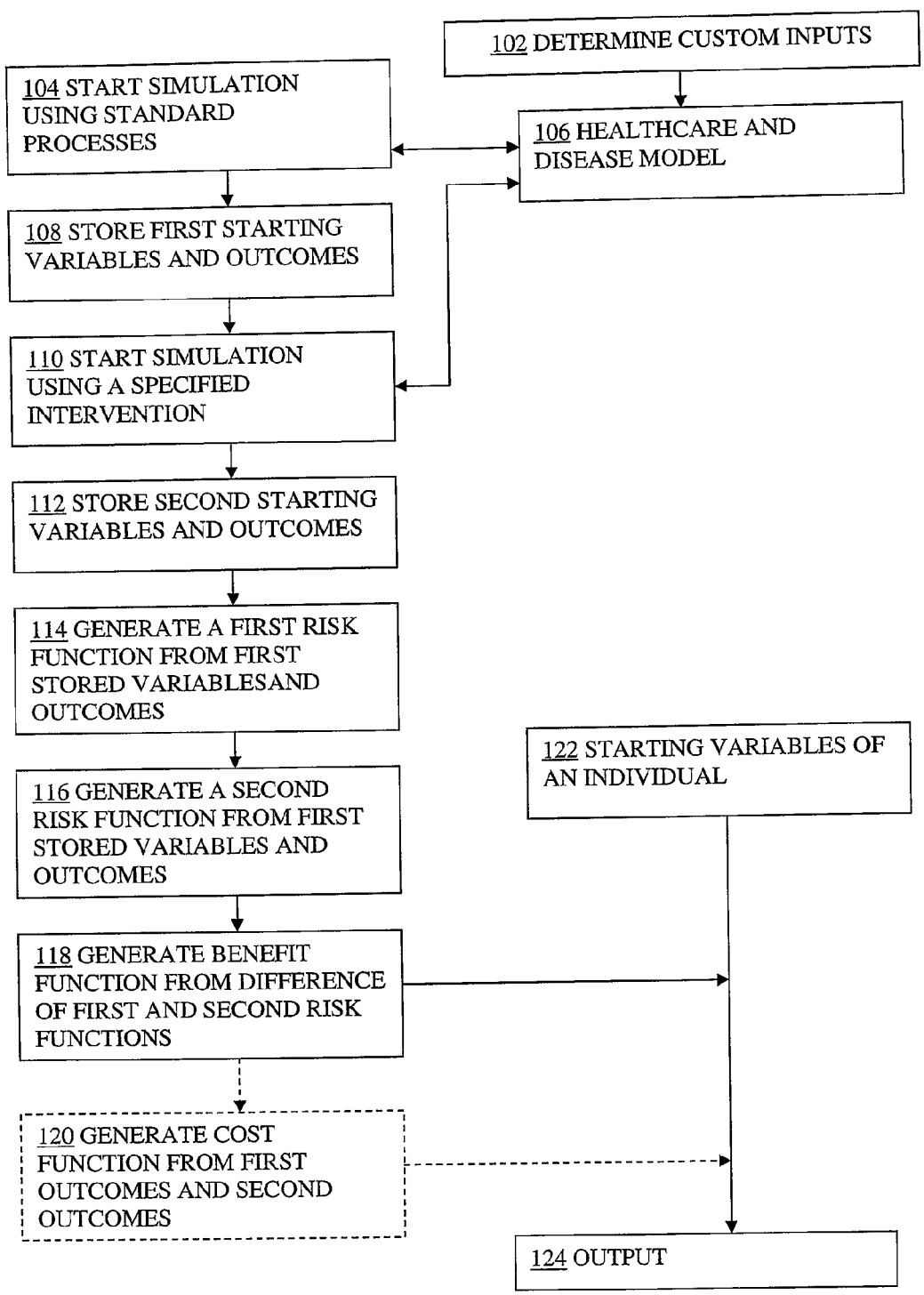
FIG. 1A illustrates a process of computing the benefit of an intervention on an individual basis.

Approaches for estimating healthcare costs and benefits for individuals are described. In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention. Embodiments are described herein according to the following outline:

1.0 General Overview
2.0 Functional Overview
3.0 Output Techniques
4.0 Implementation Mechanisms—Hardware Overview
5.0 Extensions and Alternatives

1.0 General Overview

In an embodiment, a computer-implemented method comprises receiving input data comprising healthcare costs, processes, and a population; receiving, for a first simulation on a first set of simulated subjects reflecting the population, a first set of outcome data, comprising, in part, first risk outcome values; storing a first set of initial variables and, for each simulated subject, corresponding first outcome data from the first set of outcome data; receiving, for a second simulation on a second set of simulated subjects wherein said second simulation the healthcare processes contain at least one additional healthcare intervention not included in the processes for the first simulation, a second set of outcome data, comprising, in part, second risk outcome values associated with the additional intervention; storing a second set of initial variables and, for each simulated subject, corresponding second outcome data from the second set of outcome data; determining, from the stored first set of initial variables and from the corresponding first outcome data for each simulated subject, a first risk function that describes a first risk under the first set of processes; determining, from the stored second set of initial variables and from the corresponding second outcome data for each simulated subject, a second risk function that describes a second risk under the second set of processes containing at least one additional intervention; and deriving a benefit function that represents a benefit of the intervention by subtracting the second risk function from the first risk function.

In various embodiments, defining outcome functions for benefit or cost may comprise determining a first function and a second function and obtaining a difference, as described above, or determining the difference between the first and second outcomes for each subject and deriving a function that describes the difference. Generally, these approaches are interchangeable based on the dependence of the data on the variables, the amount of noise in the data and the particular fitting methods being used in any given situation. For purposes of illustrating a clear example, this document describes one method for benefit and the other for cost, but in alternative embodiments either approach may be used in any situation.

In an embodiment, a method further comprises wherein receiving a first set of outcome data, comprising, in part, first risk outcome values, further comprises receiving a first set of outcome data, comprising, in part, first risk outcome values and first net cost outcomes values; wherein receiving a second set of outcome data, comprising, in part, second risk outcome values associated with the intervention, further comprises receiving a second set of outcome data, comprising, in part, second risk outcome values and second net cost outcome values associated with the intervention; and determining, for each subject, a difference value of the corresponding first net cost outcome values and the corresponding second net cost outcome values, and deriving, from the difference value for each subject, a net cost function that describes the net cost of the intervention.

In an embodiment, a method further comprises applying, for an input subject having associated initial values, the benefit function using the associated initial variables and generating a predicted benefit value of the intervention for the input subject; optionally applying, for the input subject, the net cost function using the associated initial variables and generating a predicted net cost value of the intervention for the input subject; and storing the predicted benefit value for the intervention and, optionally, the predicted net cost value for the intervention for post-processing.

In an embodiment, a method further comprises determining the first risk function and determining the second risk function or determining the first net cost function and determining the second net cost function comprise applying one or more regression methods including, but not limited to, generalized linear and nonlinear regressions, logistic and Poisson regressions, supervised machine learning algorithms (e.g., neural networks, support vector machines), and other methods (response surface modeling, multivariate adaptive regression splines). In an embodiment, one or more constraints may be applied. For example, an applied constraint may comprise the first risk function be greater than the second risk function, or vice-versa.

In an embodiment, the post-processing comprises determining, based in part on the predicted benefit value whether the input subject receives the intervention, is advised to receive the intervention or the status of a payer's coverage of that intervention for that subject.

In an embodiment, a method further comprises applying the benefit function and one or more intervention rules to a plurality of input subjects and outputting a list of input subjects from the plurality of input subjects to receive the intervention. In an embodiment, a method further comprises applying the benefit function and one or more ranking rules to a plurality of input subjects and outputting a ranked list of input subjects from the plurality of input subjects to receive the intervention. In an embodiment, a method further comprises applying the benefit function, the cost function, and one or more intervention rules to a plurality of input subjects, and outputting a list of input subjects from the plurality of input subjects to receive the intervention. In an embodiment, a method further comprises applying the benefit function, the cost function, and one or more ranking rules to a plurality of input subjects, and outputting a ranked list of input subjects from the plurality of input subjects to receive the intervention.

In an embodiment, a method further comprises applying the benefit function and the cost function to a ranked list of the plurality of input subjects; obtaining, for each of the plurality of input subjects, a cumulative benefit value and a cumulative cost value; displaying, on a graph having one axis represent cumulative cost values and the other axis represent cumulative benefit values, the cost values and the benefit values for each of the input subjects; and using, at a point on the graph, the slope or derivative of the curve at the point (as determined using any of several smoothing methods) to set a cost-effectiveness threshold for determining which input subjects receive the intervention. Example smoothing methods may include: average over a window of fixed size, or derivative of a function fitted to the data.

In an embodiment, the intervention is configured to represent a combination of two or more different interventions. In an embodiment, determining the first and the second risk functions comprises fitting a function to a density of the population over a space of biomarker data to determine a weighted risk function; and integrating the weighted risk function over a range of unknown variables with a subspace defined by known variables.

In an embodiment, the weighted risk function represents the likelihood of an outcome given specific biomarker data. In an embodiment, the predicted cost value is adjusted by likelihood that the input subject will change behavior towards compliance.

In an embodiment, a method further comprises creating copies of starting variables for an input subject; using an imputation method to randomly generate data to represent any missing variables of the starting variables based on the known values; applying the benefit function to the starting variables and to any generated random data to compute one or more benefit values; storing the computed one or more benefit values; repeating the generating random data step through the storing the computed one or more benefit values step for a predetermined number of times; and computing an average benefit value using the stored computed one or more benefit values.

In an embodiment, a method further comprises creating copies of starting variables for an input subject; using an imputation method to randomly generate data to represent any missing variables of the starting variables based on the known values; applying the net cost function to the starting variables and to any generated random data to compute one or more net cost values; storing the computed one or more net cost values; repeating the generating random data step through the storing the computed one or more net cost values step for a predetermined number of times; and computing an average net cost value using the stored computed one or more net cost values.

In an embodiment, an approach is provided that assists healthcare payers and planners in making cost-effective decisions about how to structure healthcare programs. Some examples of such healthcare payers and planners are employers, insurers, and public health plans. The cost and effectiveness of specific interventions can be predicted on an individual basis by using a virtual healthcare and disease model. In an embodiment, the model is an integrated simulation model of disease and the healthcare system. An example integrated healthcare and disease model is The Archimedes Model, indirect use of which is offered through consulting services by Archimedes, Inc., San Francisco, Calif.

In an embodiment, by using simulation results from an integrated healthcare and disease model as input into the present approach, it is possible to predict a broad range and number of elements of a cost benefit analysis for an individual. For example, the predicted elements can include: 1) an individual's outcomes; 2) the effect of an intervention on outcomes (the benefit); and 3) healthcare costs.

The predicted costs and benefits per individual can then be used to make decisions about the individual. For example, the predicted costs and benefits can be used to determine whether to provide a certain medication at a discounted rate to a given patient. As another example, the predicted costs and benefits predicted for a given population can be used to determine which individuals specifically should be invited to a nutrition class or weight loss program.

In an embodiment, the cost-effectiveness of an intervention is computed on an individual basis rather than population basis. In an embodiment, a targeted population is defined by choosing the individual members who will benefit the most on an individual basis using all of their available health information. By targeting such population, the cost and the effectiveness of such interventions are greatly improved compared to approaches presently in use.

Computing costs and outcomes can depend on complex interactions between multiple diseases and between an individual and the healthcare system. For example, a blood pressure appointment may result in the earlier discovery of a different disease. While such individual outcomes may be required to be discrete, in an embodiment, continuous measurements of risk, change in risk—that is, benefit—and average cost are computed by averaging over the outcomes of many similar individuals. In an embodiment, the methods described herein applied to output from a fully integrated and realistic model of multiple diseases and the healthcare system will capture these interactions. Simplified approaches that are limited to a single disease or leave out major aspects of disease progression or the healthcare system may have less effective results.

The approach herein differs from traditional risk calculators. While risk calculators assess only the risk of a health outcome, the approach herein can assess net benefit, i.e. change in risk, due to an intervention for an individual. Additionally, the approach herein can compute the change in net cost including cost savings from prevention as well as cost of treatment. When risk calculators are used for the purpose of selecting populations for treatment there is often an implicit assumption that the benefit and cost savings will be proportional to the risk. However, such an assumption generally is false.

Furthermore, risk calculators are generally derived from statistical analysis of a longitudinal data set and have a number of associated limitations. For example, in a purely statistical model, the size of the dataset limits the number of variables that can be fitted reasonably. In contrast, in an embodiment of the present approach, a framework of a physiological model is used. The applied physiological model allows more variables to be included in the physiological model and allows combining information from different sources. Some examples of different sources are cost and outcomes data that are rarely found well represented in a same dataset.

The approach herein can evaluate cost and effectiveness of various guidelines on a population. The approach can then estimate the benefit and cost of a particular intervention on an individual so that choices can be made optimally.

2.0 Functional Overview

FIG. 1A illustrates a process of computing benefit of an intervention on an individual basis in an embodiment.

At block 102, custom inputs are configured for a particular run of data. Custom inputs can reflect a population, costs, and processes of a healthcare system. In an embodiment, a population is representative of a superset from which a particular individual's population may be drawn. For example, the custom inputs might represent characteristics of a group of people in a particular region of a country, or in a particular age bracket, or a population in a particular country having specified physiology, disease, and medical history. The custom inputs may define characteristics of a relatively large population of individuals; however the number of individuals in a population may vary.

In an embodiment, the custom inputs are received from a healthcare payer organization and relate to cost structure, criteria for cost effectiveness, and information on members. Each individual member is defined by age, gender, race, biomarkers, medications, previous history, and related data. In an embodiment, the approach performs a ranking of members in which the interventions for members are ranked by benefit. As well, in an embodiment, the approach herein may determine which interventions are cost effective for each member and provide a ranking of members in which the interventions for members are ranked by cost-effectiveness. For example, for each person a mathematical model can compute outcomes indicating a reduction in the chance of adverse medical outcomes. As well, the model may compute a cost difference as a result of applying a particular intervention. In this context, "intervention" refers to preventive steps such as initiating cholesterol-lowering medication, blood pressure medication, weight loss, aspirin, stopping smoking, etc. The term "adverse medical outcomes" refers to health occurrences that are undesirable or to be avoided, such as bypass surgery, pacemaker implantation, transplant, amputation, etc.

The custom inputs are provided to a healthcare and disease model 106. An example healthcare and disease model is The Archimedes Model, which is commercially available from Archimedes, Inc., San Francisco, Calif. However, other healthcare and disease models may be used.

The model 106 comprises a healthcare and disease simulation model that reflects a population, costs, and processes of a healthcare system. The modeled populations can be quite specific to payers, such as for example, Medicare. The modeled costs can vary by country, region, and medical delivery system, and the modeled processes can differ as well; for example, different countries, hospitals, and even doctors vary in their likelihood to perform a coronary bypass.

In an embodiment, model 106 is a deep, full-scale simulation model of a health care system. The model is physiology-based, comprehensive, and clinically and administratively detailed. In an embodiment, healthcare and disease model 106 comprises one or more computers that host one or more computer programs or other software elements, coupled to a data repository, and configured to perform computer-based simulation and modeling of real-world healthcare processes including human physiology, physician-patient interactions, treatment, outcomes, and care processes.

Figure 6:
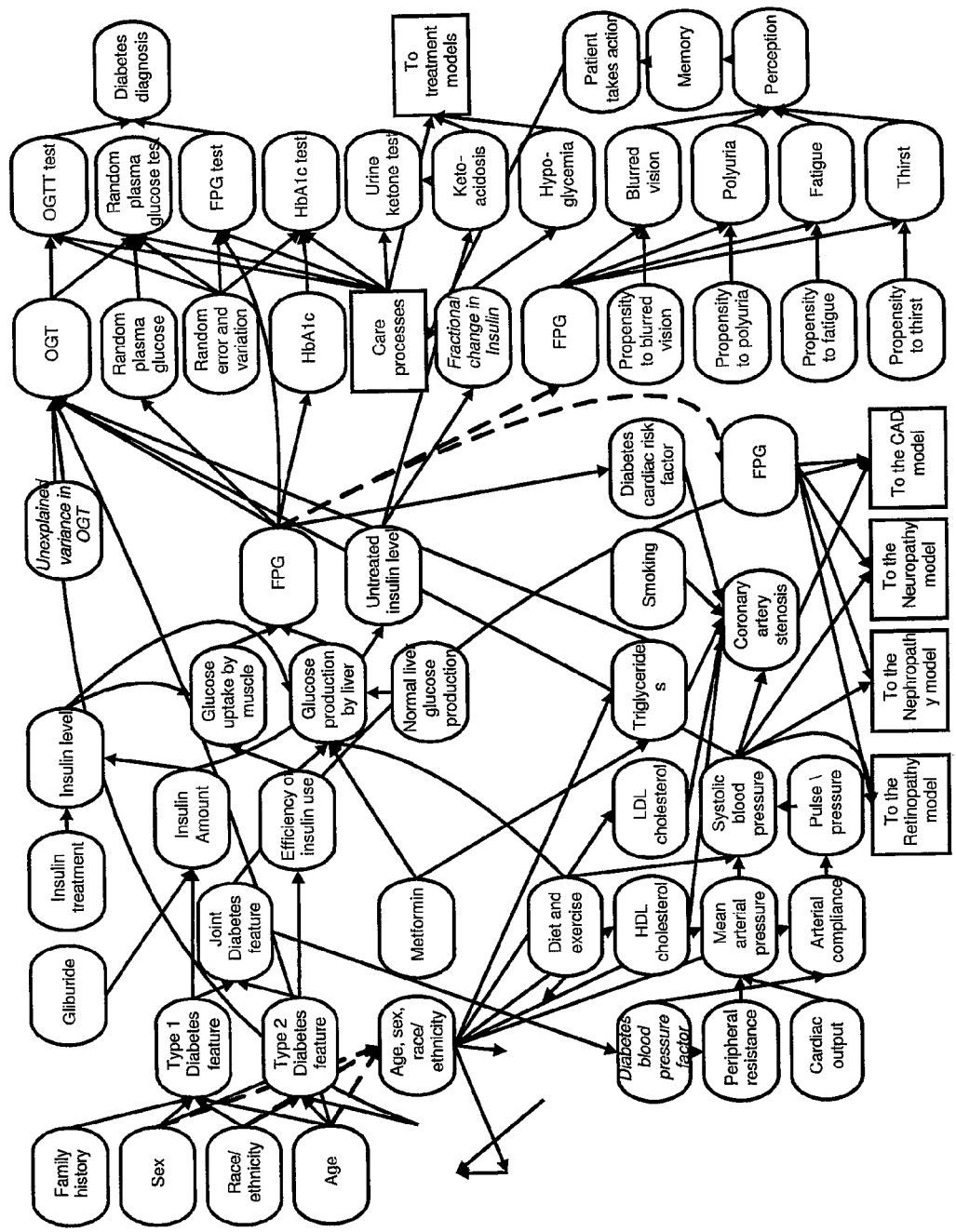
FIG. 6 illustrates example variables and equations that can model individuals, physiology, and healthcare processes.

The model 106 includes a data repository that stores data representing actual characteristics of a large number of simulated or virtual people, each of which is modeled in detail in terms of physiology, disease, medical history, and other factors. For example, each virtual person comprises a programmatic object that includes a programmatic model of major organ systems and the effect of biochemical processes and diseases. For example, to facilitate evaluation of outcomes relating to diabetes and similar conditions, each virtual person includes a virtual liver, pancreas, and circulatory system; the effects of hepatic glucose production, uptake of glucose by fat, uptake of glucose by muscle, intake of sugars by the gut, effects of insulin production, and the interaction of beta cells are modeled programmatically and mathematically so that outcomes based on many different interventions can be determined. FIG. 6 illustrates example variables and dependencies that can model individuals, physiology, and healthcare processes. All such variables and dependencies exist in each virtual person, and there may be thousands of virtual persons, each different in specific values for the variables and dependencies.

In an embodiment, model 106 supports making copies of particular individuals in a population, at a high level of clinical detail and with various specific attributes. For example, the US population, the Texas Medicaid population, the Florida Medicare population, or the population of employees of a particular corporation or entity may be modeled.

In an embodiment, model 106 is clinically and administratively detailed by representing the same level of detail at which real clinical, administrative and policy decisions are made. The model 106 represents in programmatic objects, variables and values the same clinical details that are used by physicians, guidelines, performance measures, and incentives, and the same logistic, utilization and cost details that are used by managers of departments, administrators of programs, and executives of companies.

In an embodiment, model 106 implements a mathematics-based simulation of healthcare processes that uses objects or other data structures representing virtual patients, virtual physiologies of the patients, virtual diseases, virtual doctors, virtual medical tests, virtual medical treatments and virtual healthcare outcomes. Thus, the simulation includes virtually all aspects of care, including members/patients, diseases, providers, interventions, facilities, equipment and supplies, policies and protocols, and finances. Each of these features is mathematically modeled in a high level of detail, attempting to reproduce the biological and clinical events at the level of detail at which physicians think and clinical management decisions are made.

In an embodiment, model 106 uses object-oriented programming techniques. The simulation uses data objects to represent simulated patients, doctors, offices, tests, equipment, and treatments. The model encompasses anatomy, physiology, pathology, signs and symptoms, tests and treatments, patient and provider behaviors, care processes used by healthcare providers and payers, and system resources. Data representing virtual patients includes data or objects representing major physical organs, including heart, lung, kidneys, liver and pancreas with all their respective parts that carry on their respective functions. Variables are continuous, such as blood pressure (BP) and cholesterol (LDL, HDL). Bodily functions are regulated in the model just as in reality. Example diseases and conditions that can be simulated include diabetes, coronary artery disease, congestive heart failure, asthma, stroke, hypertension, etc.

In an embodiment, the simulation models the effects of the physician-patient encounter so that the effects cause cascading changes throughout the model's simulated health care system.

In still another alternative, longitudinal experimental data from a controlled trial of sufficient size with sufficiently complete patient data, as well as cost data, are used in the approach herein to create prediction equations for benefit, as well as cost, rather than model 106. The treatment of the data is generally the same except that in such a trial the same person could not be used in both arms. The simulation is long enough so that even if a cross-over trial design were used the individual would not be the same individual by the time the individual participated in the other arm or simulation. In an embodiment, the number of predictive variables normally means that hundreds of thousands of simulated people should be generated to result in reasonably accurate fits of a single intervention. In an embodiment, data sufficient to analyze multiple interventions and combinations of interventions in different forms can exceed 300 million. Examples of such interventions are different blood pressure drugs in different dosages in combination with other interventions.

At block 104, the healthcare and disease simulation model is run using the custom inputs and virtual patient data and standard healthcare processes and starting variables to simulate the medical natural history of individuals from the data. As a result, the medical natural history of a large cohort of simulated individuals over a specified time course using the standard processes is simulated. An example standard healthcare process is administering a statin drug. The result of running the healthcare and disease simulation component is a set of one or more outcomes for the simulated individuals using standard processes. However, the effect of the custom inputs of block 102 is to focus or constrain operation of the model 106 to only those individuals who are described by the custom inputs, rather than all virtual people that are modeled in model 106 and its data repository.

The resulting one or more outcomes are stored along with the starting variables at block 108. In an embodiment, for each simulation of block 104 and block 110 (described below), and for each virtual individual in the simulation, starting variables and the set of outcomes are stored. In an embodiment, included in the set of outcomes are risk values for each individual, which may be used for computing benefit outcomes for each individual. In an alternative embodiment, included in the set of outcomes are costs for each individual. Examples of starting variables are, but are not limited to, demographic data, biomarkers, health history of each individual, behavior information for each individual, other data regarding health risk assessment of the individual, prescribed medication for the individual, and the length of time the medication is taken by the individual.

At block 110, the simulation is then performed a second time using modified processes and starting variables. The modified processes reflect one or more medical interventions. For example, the modified processes might reflect performing cardiac treadmill tests on patients who are not clearly indicated to need such a test or that every individual takes aspirin every day.

Performing the simulation a second time results in creating a second set of one or more outcomes for the virtual patient data as constrained by the inputs of block 102. The second one or more outcomes resulting from the second simulation and starting variables are also stored at block 112. It should be appreciated that in accordance with an embodiment, the starting variables used for the first simulation may be the same set of starting variables for the second simulation. As well, in accordance with an embodiment, the starting variables used for the first simulation may be different from the set of starting variables for the second simulation, e.g., the set of starting variables for the second simulation may represent a different set of individuals.

At block 114, a first risk function is generated from the first set of outcomes, which represent standard processes. The first risk function mathematically represents a risk of consequences to a virtual patient as constrained by the custom inputs of block 102 when the standard healthcare processes are applied. In an embodiment, a risk function is determined by fitting the data for risk under standard processes in terms of the starting variables.

In an embodiment, the risk function is fitted by using regression methods. Alternatively, other methods may be used for developing prediction equations from the healthcare and disease simulation output as described herein. Examples of regression methods comprise any method that fit approximate data. Examples of regression methods that may be applied in an embodiment comprise support vector machines, neural networks, logistic regressions, linear regressions, Poisson regressions, as well as other statistical fitting methods. Classification methods such as neural networks, support vector machines, classification and regression trees, random forest methods, and others may be used to develop a classifier for intervention. In an embodiment, one or more constraints may be applied to a regression method. For example, an applied constraint may comprise the first risk function be greater than the second risk function, or vice-versa. For example, applying such constraint may avoid obtaining a negative outcome, e.g., a negative benefit.

In an embodiment, the risk is a composite measure of outcomes. For example, a composite measure of outcomes is the probability of having a major cardiac event, such as myocardial infarction (MI), stroke, and coronary heart disease (CHD) death. Alternatively, life-years or QALYS may be used. In other situations other measures specific to the intervention may be used. An example of such outcome is retinopathy and the intervention is annual eye exams.

At block 116, a second risk function is generated from the second set of outcomes. The second risk function mathematically represents risk involved in performing the one or more interventions on the modeled population as constrained by the inputs of block 102. The second risk function may be generated using any of the approaches described above for block 114.

At block 118, the difference between the first risk function and the second risk function is computed, resulting in creating a benefit function for the one or more interventions. The benefit function mathematically represents the degree of benefit that can be expected for individuals in the modeled population if the one or more interventions are performed. In an embodiment, one or more constraints on the benefit function may be applied. For example, an applied constraint may comprise that the first risk function is greater than the second risk function, or vice-versa, e.g., so as to avoid resulting in a negative benefit.

As an alternative to block 114 through 118, the process may involve determining the difference between the first and second outcomes for each subject and deriving a function that describes the difference.

At block 120 and in accordance with an alternate embodiment, for each simulated individual used in the first simulation, net costs may also be computed and included in the first set of outcomes. For each simulated individual used in the second simulation reflecting one or more interventions, a net cost of the one or more interventions may be computed and included in the second set of outcomes. At block 120, a net cost function is generated by fitting a function to the computed difference between the first net cost and the second net cost for each simulated individual. In an embodiment, the net cost function is fitted by using regression methods as discussed above for block 114. As a result, net costs of performing the one or more interventions for individuals in the population, constrained by the custom inputs of block 102, are determined.

It should be appreciated that the resulting benefit function and, optionally, cost function, are the prediction functions used to compute the predicted benefit, and optionally, predicted cost, of an intervention for any person given the person's baseline variables.

It should be appreciated that costs and net costs may be defined in different ways by different users. For example, an implementation in a healthcare environment might comprise long-term healthcare cost. In another example, when the user is an employer, costs might include loss of productivity when an employee is ill, costs to hire a temporary worker when the employee cannot work due to the illness, etc. Costs of intervention (e.g., cost of weight-loss program, doctors' visits, diuretic treatments, smoking cessation programs, etc.) are input to the model. Net costs are derived from outcomes.

Block 122 represents starting data variables representing a particular individual. The starting variables might relate to a particular real person who is seeking healthcare of a particular kind. To determine the benefit of an intervention for that particular real person, the benefit function of block 118 is applied to the starting variables of the particular individual of block 122 to result in creating a final value representing a benefit of the intervention for that individual. To determine the cost of the intervention for the particular individual, the cost function is applied to the starting variables of the particular individual to result in a cost value of the intervention for the particular individual. Block 124 represents generating the final benefit value and the final cost value for the individual.

Figure 1B:
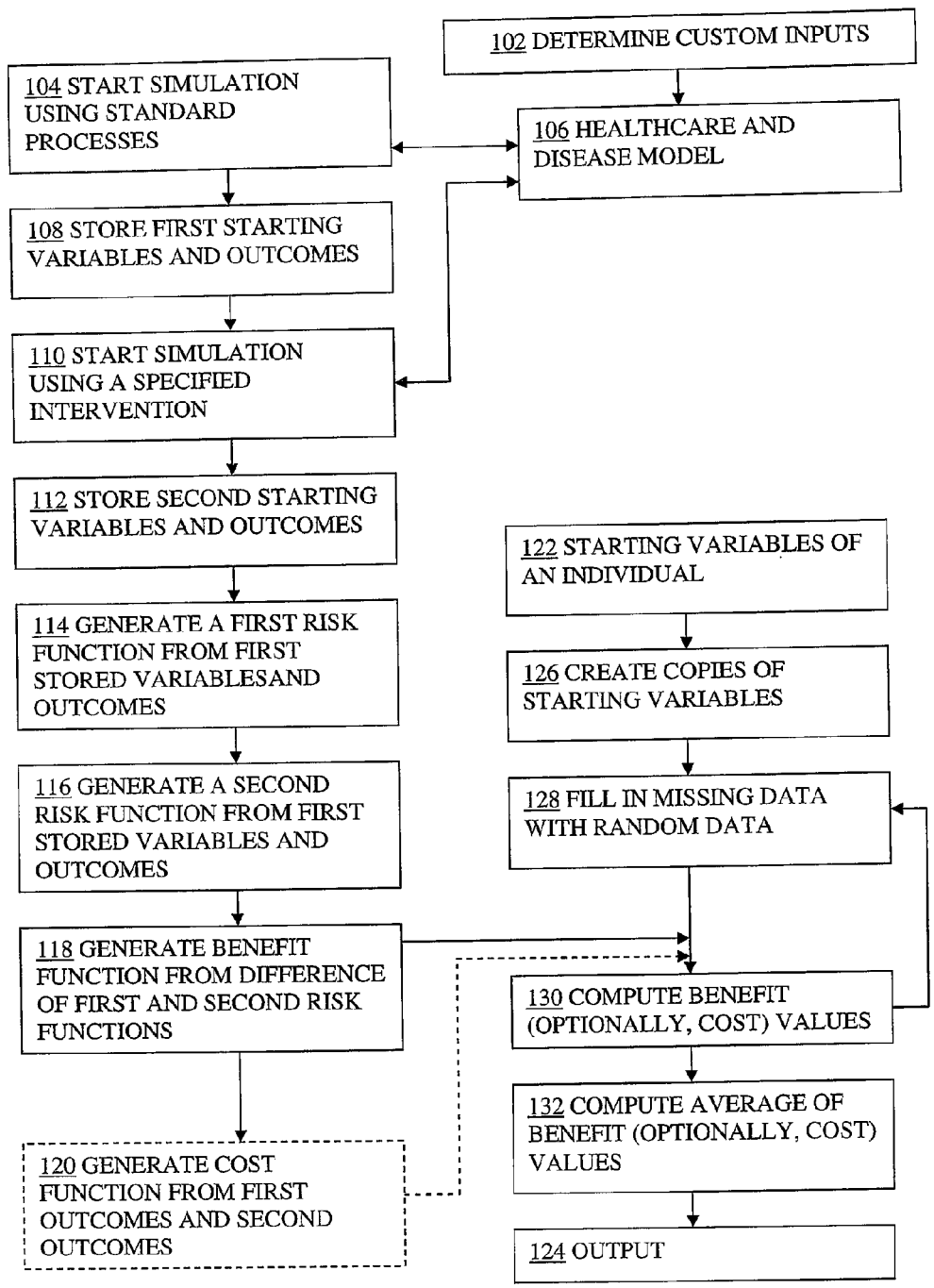
FIG. 1B illustrates a process of computing the benefit of an intervention on an individual basis.

Another embodiment can be described with reference to FIG. 1B. FIG. 1B illustrates components of FIG. 1A with additional components. As in FIG. 1A, block 122 represents starting data variables representing a particular individual. The starting variables might relate to a particular real person who is seeking healthcare of a particular kind. At block 126, copies of starting variables for an individual are made. At block 128, when data is missing for particular variables, random data for such variables are generated and used as data for the particular variables. To determine the benefit (and, optionally, cost) of an intervention for that particular real person and with that particular set of data, the benefit function of block 118 (and, optionally, the cost function) is applied to the particular set of data, comprising the starting variables and randomly generated data for missing variables, to result in creating and storing one or more final values representing a benefit (and, optionally, cost) of the intervention for that particular real person. The process returns to block 128 and is repeated many times, each time generating new random data for the missing variables. After a predetermined number of iterations of steps represented by block 128 through block 130, at block 132, the average values of the stored final values are computed to determine final benefit values (and, optionally, the final cost values) for the particular real person. Block 124 represents generating the final benefit value and, optionally, the final cost value for the individual.

In an alternative embodiment, the benefit values and, optionally, cost values, may be obtained directly from the simulation data without fitting prediction functions. In an embodiment, a more computationally expensive approach is provided. The approach involves simulating each person in the real population many times (e.g., 1,000) and obtaining benefit values, and optionally, cost values, from the average results. In another embodiment of intermediate computational complexity the average of a set of nearest neighbors is used rather than a fitted equation.

3.0 Output Techniques 3.1 Example Output Approaches

Different forms of output can correspond to different output requirements. For example, an insurance payer may request output that conforms to a rule for intervention, such as "perform any intervention that saves money in three years" or "perform any intervention that does not cost more than $10,000 per quality-adjusted life year." Based on this rule, the approach herein can decide who should get the intervention based on the predicted cost and benefit for each individual.

For example, an unranked list of individuals can be returned. In a second approach, a ranking method may be used. For example, the individuals can be ranked by cost, by benefit, or by cost-effectiveness. The receiver of the output, such as an insurance payer, may define the ranking method. The receiver then has an opportunity to determine a threshold point on the list that determines who receives the intervention and who does not.

Payers may be particularly interested in ranking individuals according to the criteria of each individual for who should receive an intervention first. Ranking enables the payers to allocate scarce resources (e.g. nurses in a call center) in the most efficient manner. Furthermore, if multiple interventions are being considered, payers can be interested in ranking the interventions by importance. In an embodiment, interventions for a single person can be ranked by the same criteria as above.

3.2 Example Graphical Output

In an embodiment, the financial impact of using the approach herein can be presented as follows. A user can run a separate simulation of individuals as a test set and show the cost and benefit that would be achieved for this population by applying the methodology. One reason for running a new simulation is to create a set of individuals that are independent of the set of individuals that was used for generating the benefit or cost functions. That is, a user simulates each individual in a control arm and an intervention arm. The difference in cost and benefit due to treatment is computed for each individual. The individuals are ranked by predicted risk or cost as described above and then graphed. In an embodiment, the impact in terms of the cost or benefit of treating a fraction of such population in the order of the ranking is graphed.

Graphical presentation of results in this manner is particularly effective because the ranking can be compared directly with other approaches for determining which individuals should receive treatment. Examples of other approaches include a random approach, ranking according to a prominent biomarker such as cholesterol (LDL), following a guideline, or ranking according to an accepted risk score such as the Framingham cardiovascular risk calculator.

A third graphical presentation involves putting cost on one axis and benefit on the other. This approach illustrates the degree to which it is possible to improve health outcomes and save money simultaneously. Because the slope or derivative of the curve at a point on the graph is cost-effectiveness, this graph is particularly useful for setting cost-effectiveness thresholds. In an embodiment, the slope may be computed by any method for estimating the slope at a point or derivative of a curve at a point, e.g., $\Delta x/\Delta y$.

Figure 2:
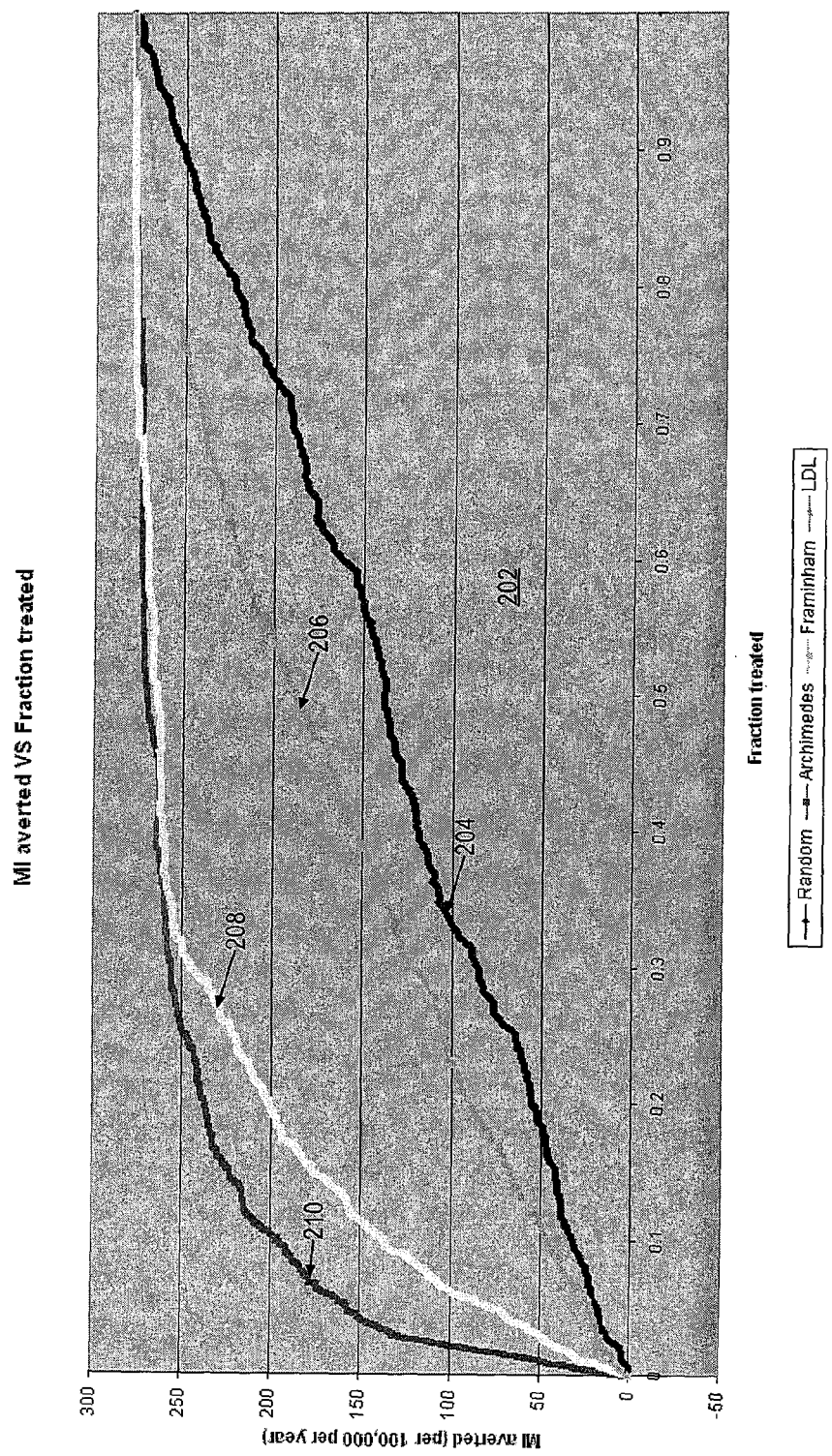
FIG. 2 is a graph of adverse medical events averted versus individuals treated illustrating the superior performance of an embodiment as compared with other approaches.
Figure 3:
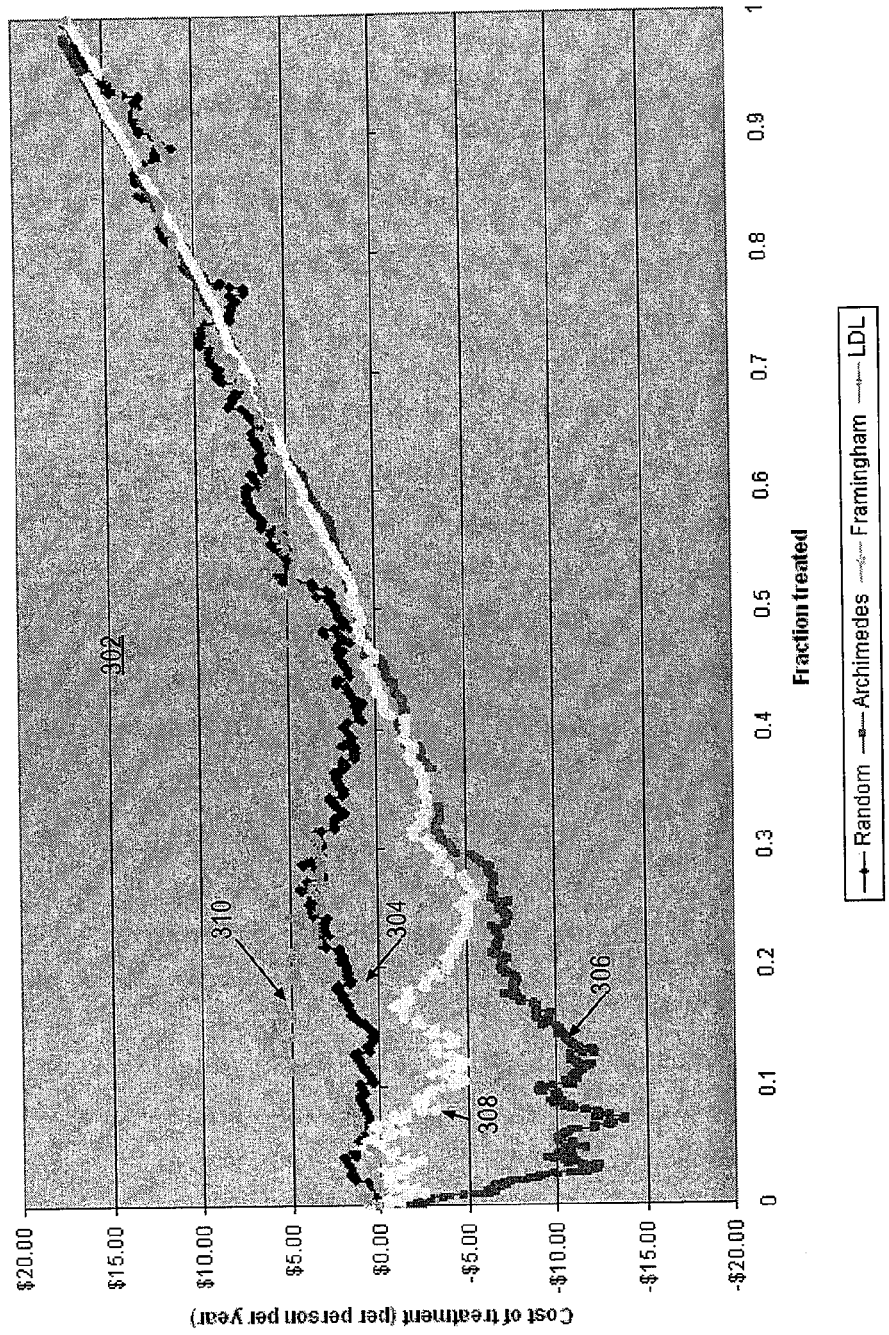
FIG. 3 is a graph of cost versus individuals treated illustrating the superior performance of an embodiment as compared with other approaches.
Figure 4:
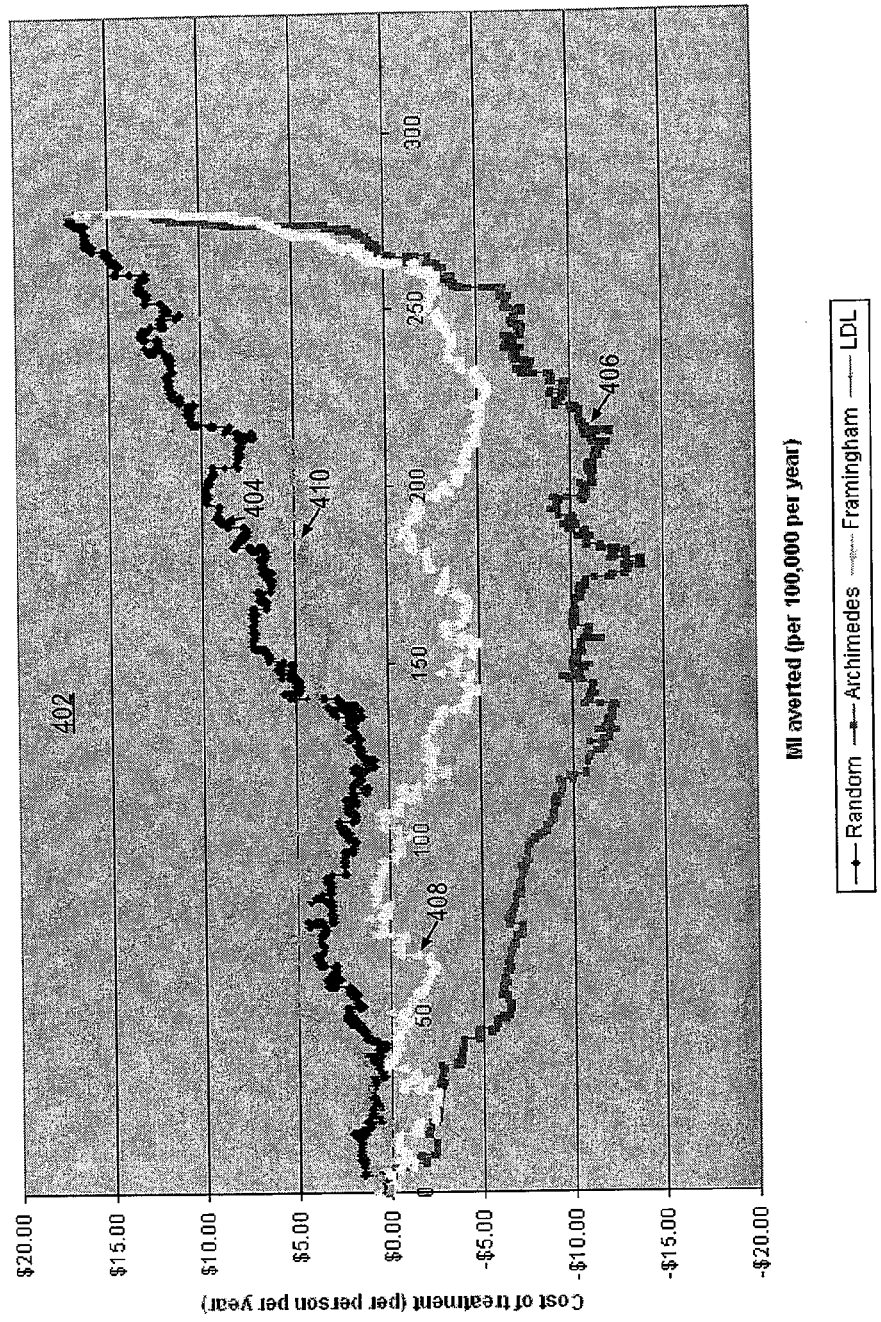
FIG. 4 is a graph of adverse medical events averted versus cost illustrating the superior performance of an embodiment as compared with other approaches.

An example embodiment uses a lovastatin ("statin") drug as an intervention. FIG. 2 is a graph of adverse medical events averted versus individuals treated illustrating the superior performance of an embodiment as compared with other approaches; FIG. 3 is a graph of cost versus individuals treated illustrating the superior performance of an embodiment as compared with other approaches; FIG. 4 is a graph of adverse medical events averted versus cost illustrating the superior performance of an embodiment as compared with other approaches.

FIG. 2 illustrates the results of treating individuals with a statin according to each of the approaches above. In graph 202 of FIG. 2, line 204 represents adverse medical events that are averted when a random choice is used to determine whether to administer a statin drug to the individuals in a particular fraction of a population. Line 206 illustrates adverse medical events that are averted when individuals who have the highest LDL are selected for treatment. Line 208 illustrates adverse medical events that are averted when a Framingham risk calculator is used to determine whether to administer a statin. Line 210 illustrates adverse medical events that are averted when the present approach is used. The position of line 210 indicates that the approach herein is superior in averting far more adverse medical events when used for even a small fraction of persons in a population.

FIG. 3 is a graph of the difference in cost between continuing with and without an intervention versus the fraction of a population of individuals who are treated. In graph 302 of FIG. 3, line 304 represents costs that are incurred for a fraction of a population when individuals are selected for treatment at random. Line 306 represents costs that are incurred for a fraction of a population when individuals are selected for treatment using the approach herein. Line 308 represents costs that are incurred for a fraction of a population when individuals are selected for treatment using a Framingham risk calculator. Line 310 represents costs that are incurred for a fraction of a population when individuals having the highest LDL are selected for treatment. Line 306 indicates that significant cost savings can result using the present approach, especially when applied to a small fraction of a population. FIG. 4 is a graph of the adverse medical events averted versus the cost of treatment. In graph 402, line 404 represents using a random approach to determine whether to apply treatment; line 406 represents using the approach herein to determine whether to apply treatment; line 408 represents use of a Framingham risk calculator to determine whether to apply treatment; and line 410 represents using the highest LDL to determine whether to apply treatment.

In an embodiment, input variables describe each individual by using the individual's age, gender, race, biomarkers, medications, and previous history. For each person the methodology is used to compute outcomes (e.g. reduction in chance of a myocardial infarction), cost difference as a result of treatment, cost of treatment (e.g. the drug, tests, and visits), and cost of not treating (MIs, strokes, etc.). A ranking can be used to treat individuals who will receive the most improved outcomes per dollar spent, based on the model 106. In an embodiment, individuals who receive the most improved outcomes per dollar spent are treated. Examples of medical interventions are, but are not limited to, blood pressure, glucose control, smoking, weight loss, blood test, and case management (e.g., for congestive heart failure.)

While the Framingham equation and Framingham risk calculators predict risk with no intervention, the present approach predicts risk, outcomes of intervention, and cost. Thus, improvement in outcomes is not necessarily proportional to risk. For example, the approach herein may take into account additional risk factors such as a previous MI, angina, and continuous diabetes.

Further, cost is important and is considered in the present approach. In the approach herein, three ingredients of cost effectiveness are modeled: risk, benefit, and cost, all on an individual basis. Therefore, by using realistic detail, multiple diseases, outcomes, and costs are comprehensively captured.

Figure 7:
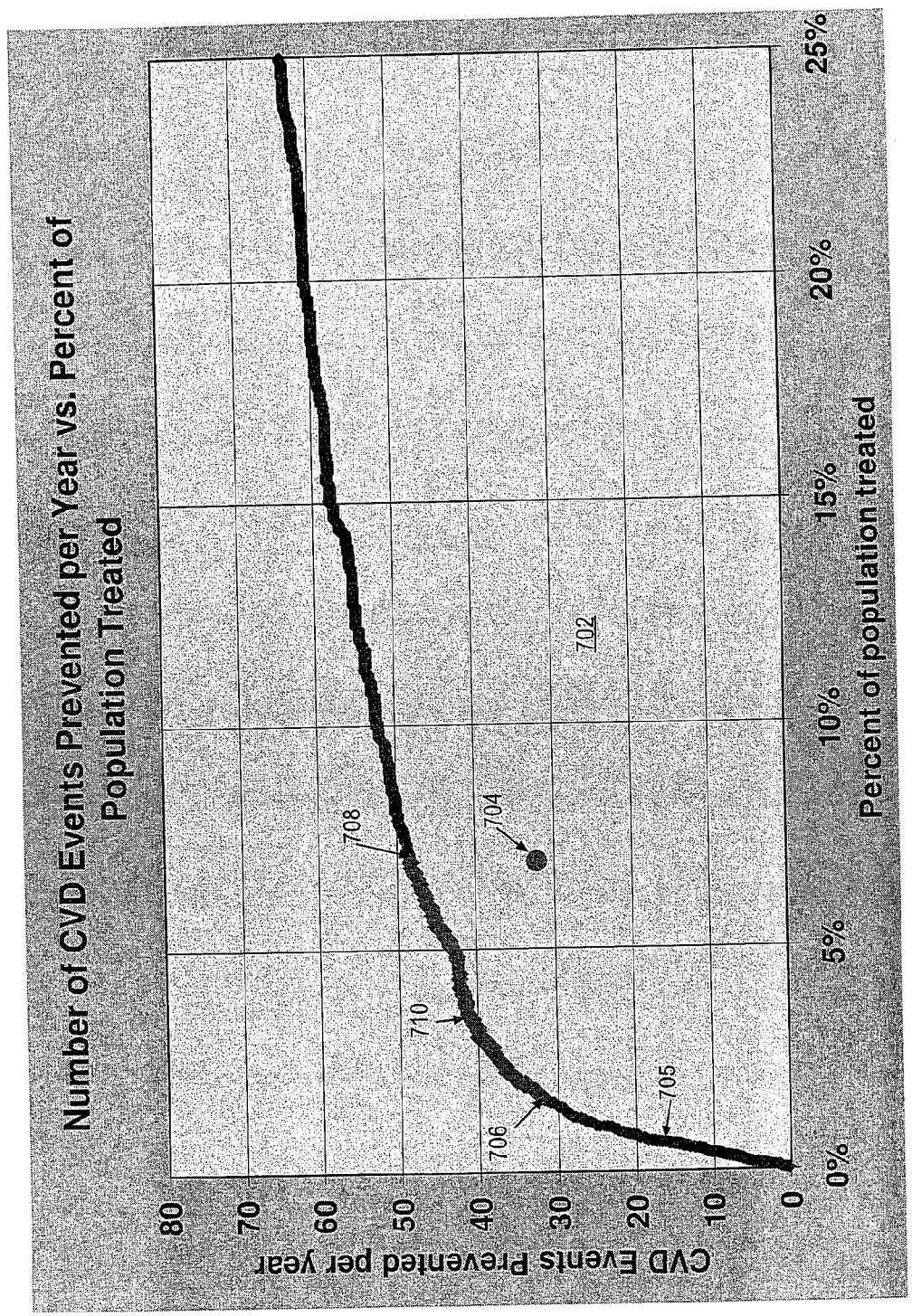
FIG. 7 is a graph of adverse medical events averted versus individuals treated illustrating the optimal zone whereby quality is improved and costs are saved.

FIG. 7 is a graph of a number of cardiovascular disease events that may be prevented per year compared to a percentage of a population that is treated in a particular way. FIG. 7 illustrates using the present approach to determine how certain cardiovascular disease interventions may affect a population. For example, to develop the data shown in FIG. 7, the model 106 may used to simulate a population of 30,000 people who are similar to a particular company's actual employee population of adults aged 20 to 80. The model may be used to simulate using the Adult Treatment Panel III (ATP III) of the National Cholesterol Education Program guidelines to determine whether to treat individuals for cardiovascular disease, and applying such decisions to 100% of the population for 3 years. The model may be used to count all cardiovascular disease outcomes, including myocardial infarction, stroke, and death, and to measure all costs. GAP analysis with such a simulation may determine, for example, that if 6.9% of the adult population is treated, then 32 events per year are prevented, as indicated by point 704 in graph 702 of FIG. 7.

The approach herein then can be used to use all available clinical information, not just the information that is used in the ATP III guidelines, to compute for each virtual person their risk of each kind of cardiovascular disease event and how much that risk can be reduced by treatment. Further, the virtual persons can be ranked by degree of expected benefit. Line 705 of FIG. 7 indicates a number of cardiovascular disease events that may be prevented per year compared to a percentage of a population that is treated based on decisions when indicated by the model 106, as opposed to using the ATP guidelines. Point 706 on line 705 has the same Y-axis value as point 704, and point 708 has the same X-axis value as point 704. Point 708 indicates that by applying treatment according to the model 106, a payer can treat the same number of people but get 50% more benefit. Similarly, point 706 indicates that the same benefit as point 704 can be achieved by treating only one-fourth of the number of people. Thus, any point on an optimal zone represented by line segment 710 between points 706, 708 creates more quality and saves more money. The present approach facilitates performing such cost-benefit analysis in ways that are not possible in prior approaches. The results can better determine who should receive special care beyond what current systems are providing.

The specific principles described above for FIG. 7 relate only to GAP analysis of the ATP guidelines, only one population, only partial data from that population, only one setting, and only cardiovascular disease. However, embodiments are not limited to these conditions and embodiments can be applied in the same way for many other populations, conditions, interventions, and guidelines. For example, different populations could take into account Medicare versus commercial payers, various geographic regions, or particular accounts. Conditions could include diabetes, congestive heart failure, asthma, or others. Interventions could include glucose, obesity, smoking, LDL and BP for diabetes, aspirin, triglycerides, HDL, pre-diabetes, eye and foot examinations, and others. Combinations of interventions can be evaluated.

3.3 Analysis of Combined Interventions

Healthcare providers may treat individuals with more than one intervention simultaneously. Depending on how the interventions, diseases, and healthcare processes interact, the resulting effect may or may not be the same as any combination of the two or more separate effects. The product of the relative risks might be an expected outcome when the interventions are independent.

In an embodiment, an additional intervention is simulated as a combination of two interventions. An example of two interventions is: give statins and give blood pressure medication. The payer can then choose the single intervention or combination of interventions whose predicted outcome was the best. The effect of using an intervention that itself is a combined intervention on total benefits and savings can be graphically represented. The payer can choose for each person in a "test" simulation the combination of interventions with the best predicted results, ranking, and graphing by this prediction.

3.4 Consideration of Missing Data

Healthcare payers can possess data on risk factors of a significant subset of the payer's individual members. The data of payers usually is incomplete, but it is desirable to estimate risk even when data is missing. In an embodiment, a function is fitted to population density over a space of biomarkers. By using fast methods, weighted risk is integrated over a range of unknown variables within a subspace defined by the known variables.

In an embodiment, diagnoses are translated to probable biomarker data. In an embodiment, a weighting function, estimating the likelihood of an outcome given biomarker data, is employed. Examples of an outcome are a condition, diagnosis, and QALYS.

4.0 Implementation Mechanics

Hardware Overview

Figure 5:
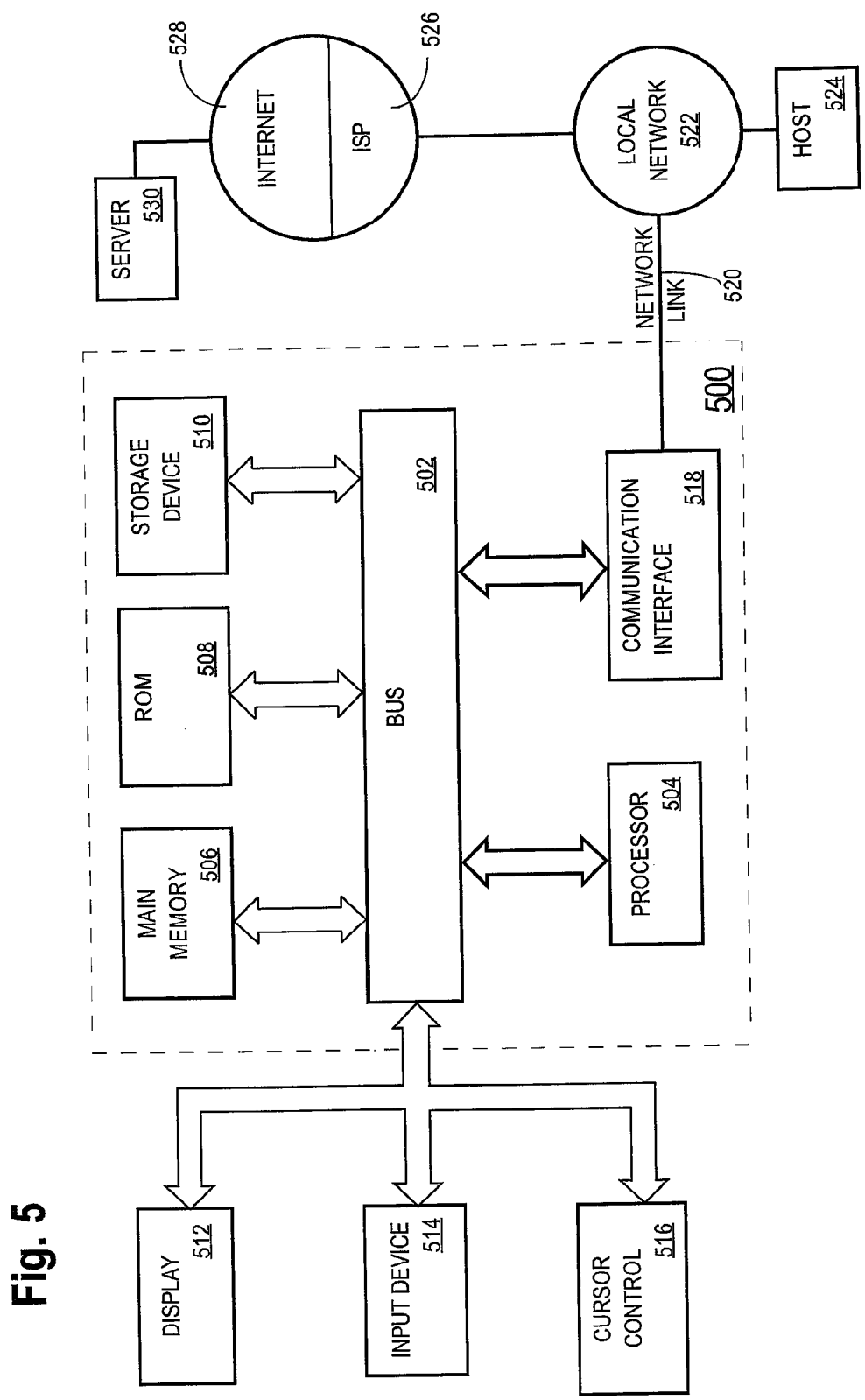
FIG. 5 is a block diagram illustrating a computer system upon which an embodiment of the invention may be implemented.

FIG. 5 is a block diagram that illustrates a computer system 500 upon which an embodiment of the invention may be implemented. Computer system 500 includes a bus 502 or other communication mechanism for communicating information, and a processor 504 coupled with bus 502 for processing information. Computer system 500 also includes a main memory 506, such as a random access memory (RAM) or other dynamic storage device, coupled to bus 502 for storing information and instructions to be executed by processor 504. Main memory 506 also may be used for storing temporary variables or other intermediate information during execution of instructions to be executed by processor 504. Computer system 500 further includes a read only memory (ROM) 508 or other static storage device coupled to bus 502 for storing static information and instructions for processor 504. A storage device 510, such as a magnetic disk or optical disk, is provided and coupled to bus 502 for storing information and instructions.

Computer system 500 may be coupled via bus 502 to a display 512, such as a cathode ray tube (CRT), for displaying information to a computer user. An input device 514, including alphanumeric and other keys, is coupled to bus 502 for communicating information and command selections to processor 504. Another type of user input device is cursor control 516, such as a mouse, a trackball, or cursor direction keys for communicating direction information and command selections to processor 504 and for controlling cursor movement on display 512. This input device typically has two degrees of freedom in two axes, a first axis (e.g., x) and a second axis (e.g., y), that allows the device to specify positions in a plane.

The invention is related to the use of computer system 500 for implementing the techniques described herein. According to an embodiment of the invention, those techniques are performed by computer system 500 in response to processor 504 executing one or more sequences of one or more instructions contained in main memory 506. Such instructions may be read into main memory 506 from another machine-readable medium, such as storage device 510. Execution of the sequences of instructions contained in main memory 506 causes processor 504 to perform the process steps described herein. In alternative embodiments, hard-wired circuitry may be used in place of or in combination with software instructions to implement the invention. Thus, embodiments of the invention are not limited to any specific combination of hardware circuitry and software.

The term "machine-readable medium" as used herein refers to any medium that participates in providing data that causes a machine to operate in a specific fashion. In an embodiment implemented using computer system 500, various machine-readable media are involved, for example, in providing instructions to processor 504 for execution. Such a medium may take many forms, including but not limited to storage media and transmission media. Storage media includes both non-volatile media and volatile media. Non-volatile media includes, for example, optical or magnetic disks, such as storage device 510. Volatile media includes dynamic memory, such as main memory 506. Transmission media includes coaxial cables, copper wire and fiber optics, including the wires that comprise bus 502. Transmission media can also take the form of acoustic or light waves, such as those generated during radio-wave and infra-red data communications. All such media must be tangible to enable the instructions carried by the media to be detected by a physical mechanism that reads the instructions into a machine.

Common forms of machine-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of machine-readable media may be involved in carrying one or more sequences of one or more instructions to processor 504 for execution. For example, the instructions may initially be carried on a magnetic disk of a remote computer. The remote computer can load the instructions into its dynamic memory and send the instructions over a telephone line using a modem. A modem local to computer system 500 can receive the data on the telephone line and use an infra-red transmitter to convert the data to an infra-red signal. An infra-red detector can receive the data carried in the infra-red signal and appropriate circuitry can place the data on bus 502. Bus 502 carries the data to main memory 506, from which processor 504 retrieves and executes the instructions. The instructions received by main memory 506 may optionally be stored on storage device 510 either before or after execution by processor 504.

Computer system 500 also includes a communication interface 518 coupled to bus 502. Communication interface 518 provides a two-way data communication coupling to a network link 520 that is connected to a local network 522. For example, communication interface 518 may be an integrated services digital network (ISDN) card or a modem to provide a data communication connection to a corresponding type of telephone line. As another example, communication interface 518 may be a local area network (LAN) card to provide a data communication connection to a compatible LAN. Wireless links may also be implemented. In any such implementation, communication interface 518 sends and receives electrical, electromagnetic or optical signals that carry digital data streams representing various types of information.

Network link 520 typically provides data communication through one or more networks to other data devices. For example, network link 520 may provide a connection through local network 522 to a host computer 524 or to data equipment operated by an Internet Service Provider (ISP) 526. ISP 526 in turn provides data communication services through the world wide packet data communication network now commonly referred to as the "Internet" 528. Local network 522 and Internet 528 both use electrical, electromagnetic or optical signals that carry digital data streams. The signals through the various networks and the signals on network link 520 and through communication interface 518, which carry the digital data to and from computer system 500, are exemplary forms of carrier waves transporting the information.

Computer system 500 can send messages and receive data, including program code, through the network(s), network link 520 and communication interface 518. In the Internet example, a server 530 might transmit a requested code for an application program through Internet 528, ISP 526, local network 522 and communication interface 518.

The received code may be executed by processor 504 as it is received, and/or stored in storage device 510, or other non-volatile storage for later execution. In this manner, computer system 500 may obtain application code in the form of a carrier wave.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

5.0 Extensions and Alternatives

5.1 Other Forms of Result

In an embodiment, another variation on the methodology can achieve an equivalent result. The embodiment uses a different functional form for fitting a function to a multidimensional surface. The surface separates the population upon which to be intervened according to the clients rule from a non-intervention population. An example surface is the surface for which net cost of the intervention is zero. The sign of an inequality is used to determine whether or not to intervene.

5.2 Modeling Compliance

In an embodiment, the expected cost savings are adjusted by the likelihood that a particular individual will change behavior or compliance. For example, pharmacy benefits management (PBM) data can be compared to prescriptions in estimating compliance. Expected savings are greater for members with greater compliance.

5.3 Alternative Method for Simulating Individiduals

The somewhat rare occurrence of major and costly health outcomes leads to a rather "rough" data surface of cost and benefit points corresponding to simulated individuals. In an alternative embodiment, the simulation of each "person" is repeated many times using different random risk values. Then, the costs and benefits for each "person" across his different incarnations are averaged. The result in a data point surface that should be much smoother, easier to fit, and less likely to have aberrant behavior at the edges.

What is claimed is:

1. A method comprising:
   determining a plurality of healthcare interventions for use in simulating effects on each subject of a set of simulated subjects;
   for each subject of the set of simulated subjects:
      for each intervention of the plurality of healthcare interventions, generating a set of healthcare outcome data that comprises, at least in part, risk outcome values and benefits outcome values, using computer simulation of effects of the plurality of healthcare interventions on each subject of the set of simulated subjects;
      wherein a particular risk outcome value, determined for a particular subject and for a particular intervention, indicates a particular risk that the particular subject subjected to the particular intervention would develop a particular disease;
      wherein a particular benefit outcome value, determined for the particular subject and for the particular intervention, indicates a particular degree of benefit that can be expected for the particular subject if the particular subject is subjected to the particular intervention;
   for the particular subject of the set of simulated subjects, determining, using a computing device, risk differences between the risk outcome values of a plurality of sets of outcome data that were generated for the subject of the set of simulated subjects for each of the plurality of healthcare interventions, and benefit differences between the benefits outcome values of a plurality of sets of outcome data that were generated for the subject of the set of simulated subjects for each of the plurality of healthcare interventions;
   for the particular subject of the set of simulated subjects, generating one or more reports indicating the risk differences and the benefit differences;
   wherein the method is performed by one or more computing devices.

2. The method of claim 1, wherein the one or more reports indicate the risk differences between first risk outcome values based on simulating first risk effects of a first intervention of the plurality of healthcare interventions, and second risk outcome values based on simulating second risk effects of a second intervention of the plurality of healthcare interventions.

3. The method of claim 2, wherein the one or more reports indicate the benefit differences between first benefit outcome values based on simulating first benefit effects of the first intervention of the plurality of healthcare interventions, and second benefit outcome values based on simulating second benefit effects of the second intervention of the plurality of healthcare interventions.

4. The method of claim 1, comprising:
   generating one or more sets of outcome data comprising at least in part risk, outcome measures and benefits outcome measures that are determined as if no intervention was applied to each subject;
   for each subject, generating one or more outcome summaries indicating whether any of the plurality of healthcare interventions provides particular risk outcome values that exceed risk outcome measures;
   for each subject, generating one or more benefit summaries indicating whether any of the plurality of healthcare interventions provides particular benefit outcome values that exceed the benefit outcome measures.

5. The method of claim 4, comprising causing generating any one of a graphical user interface (GUI) on a computer display depicting the one or more reports and the one or more outcome summaries, or an electronic message comprising the one or more reports and the one or more outcome summaries.

6. A non-transitory computer-readable storage medium, storing one or more instructions which, when executed by one or more processors, cause:
   determining a plurality of healthcare interventions for use in simulating effects on each subject of a set of simulated subjects;
   for each subject of the set of simulated subjects:
      for each intervention of the plurality of healthcare interventions, generating a set of healthcare outcome data that comprises, at least in part, risk outcome values and benefits outcome values, using computer simulation of effects of the plurality of healthcare interventions on each subject of the set of simulated subjects;
      wherein a particular risk outcome value, determined for a particular subject and for a particular intervention, indicates a particular risk that the particular subject subjected to the particular intervention would develop a particular disease;
      wherein a particular benefit outcome value, determined for the particular subject and for the particular intervention, indicates a particular degree of benefit that can be expected for the particular subject if the particular subject is subjected to the particular intervention;

for the particular subject of the set of simulated subjects, determining, using a computing device, risk differences between the risk outcome values of a plurality of sets of outcome data that were generated for the subject of the set of simulated subjects for each of the plurality of healthcare interventions, and benefit differences between the benefits outcome values of a plurality of sets of outcome data that were generated for the subject of the set of simulated subjects for each of the plurality of healthcare interventions;

for the particular subject of the set of simulated subjects, generating one or more reports indicating the risk differences and the benefit differences.

7. The non-transitory computer-readable storage medium of claim 6,
wherein the one or more reports indicate the risk differences between first risk outcome values based on simulating first risk effects of a first intervention of the plurality of healthcare interventions, and second risk outcome values based on simulating second risk effects of a second intervention of the plurality of healthcare interventions.

8. The non-transitory computer-readable storage medium of claim 7,
wherein the one or more reports indicate the benefit differences between first benefit outcome values based on simulating first benefit effects of the first intervention of the plurality of healthcare interventions, and second benefit outcome values based on simulating second benefit effects of the second intervention of the plurality of healthcare interventions.

9. The non-transitory computer-readable storage medium of claim 8, comprising instructions which, when executed, cause:
generating one or more sets of outcome data comprising at least in part risk, outcome measures and benefits outcome measures that are determined as if no intervention was applied to each subject;
for each subject, generating one or more outcome summaries indicating whether any of the plurality of healthcare interventions provides particular risk outcome values that exceed risk outcome measures;
for each subject, generating one or more benefit summaries indicating whether any of the plurality of healthcare interventions provides particular benefit outcome values that exceed the benefit outcome measures.

10. The non-transitory computer-readable storage medium of claim 9, comprising instructions which, when executed, cause generating any one of a graphical user interface (GUI) on a computer display depicting the one or more reports and the one or more outcome summaries, or an electronic message comprising the one or more reports and the one or more outcome summaries.

11. A method comprising:
determining a plurality of healthcare interventions and a set of simulated subjects of the healthcare interventions;
performing computer simulation of effects of each of the plurality of healthcare interventions on each subject of the set of simulated subjects;
receiving, from a plurality of simulations performed on the set of simulated subjects, a plurality of sets of outcome data;
wherein a particular risk outcome value, of the plurality of sets of outcome data, is determined for a particular subject and for a particular intervention, and indicates a particular risk that the particular subject subjected to the particular intervention would develop a particular disease;
applying a benefit function to the plurality of sets of outcome data for the set of simulated subjects to determine a first ranked list of subjects that is ranked according to a benefit value, from a plurality of benefit outcome values, expected when some of the plurality of healthcare interventions are applied;
wherein a particular benefit outcome value, of the plurality of benefit outcome values, is determined for the particular subject and for the particular intervention, and indicates a particular degree of benefit that can be expected for the particular subject if the particular subject is subjected to the particular intervention;
using a computing device, applying a net cost function to the plurality of sets of outcome data for the set of simulated subjects to determine a second ranked list of subjects that is ranked according to a net cost value expected when some of the plurality of healthcare interventions are applied;
determining, using the first ranked list and the second ranked list, a set of individuals who receive most improved outcomes compared to a cost;
wherein the method is performed by one or more computing devices.

12. The method as recited in claim 11, wherein the benefit function represents benefit effects obtained when a particular intervention, of the plurality of healthcare interventions, is simulated on the particular subject from the set of simulated subjects.

13. The method as recited in claim 11, wherein the net cost function represents net cost effects obtained when a particular intervention, of the plurality of healthcare interventions, is simulated on the particular subject from the set of simulated subjects.

14. The method as recited in claim 11, comprising:
for a particular intervention, of the plurality of healthcare interventions, and the particular subject, of the set of simulated subjects, having associated initial values:
applying the benefit function to the associated initial values and generating a predicted benefit value that is obtainable by simulating the particular intervention on the particular subject;
applying the net cost function to the associated initial values and generating a predicted net cost value that is obtainable by simulating the particular intervention on the particular subject;
storing the predicted benefit value and the predicted net cost value for the particular intervention.

15. The method as recited in claim 14, comprising applying one or more regression methods when generating the predicted benefit value and generating the predicted net cost value, wherein the one or more regression methods are selected from: generalized linear and nonlinear regressions, logistic and Poisson regressions, supervised machine learning algorithms, neural networks, support vector machines, response surface modeling, and multivariate adaptive regression splines.

16. A non-transitory computer-readable storage medium, storing one or more instructions which, when executed by one or more processors, cause:
determining a plurality of healthcare interventions and a set of simulated subjects of the healthcare interventions;
performing computer simulation of effects of each of the plurality of healthcare interventions on each subject of the set of simulated subjects;

receiving, from a plurality of simulations performed on the set of simulated subjects, a plurality of sets of outcome data;

wherein a particular risk outcome value, of the plurality of sets of outcome data, is determined for a particular subject and for a particular intervention, and indicates a particular risk that the particular subject subjected to the particular intervention would develop a particular disease;

applying a benefit function to the plurality of sets of outcome data for the set of simulated subjects to determine a first ranked list of subjects that is ranked according to a benefit value, from a plurality of benefit outcome values, expected when some of the plurality of healthcare interventions are applied;

wherein a particular benefit outcome value, of the plurality of benefit outcome values, is determined for the particular subject and for the particular intervention, and indicates a particular degree of benefit that can be expected for the particular subject if the particular subject is subjected to the particular intervention;

applying a net cost function to the plurality of sets of outcome data for the set of simulated subjects to determine a second ranked list of subjects that is ranked according to a net cost value expected when some of the plurality of healthcare interventions are applied;

determining, using the first ranked list and the second ranked list, a set of individuals who receive most improved outcomes compared to a cost.

17. The non-transitory computer-readable storage medium as recited in claim 16, wherein the benefit function represents benefit effects obtained when a particular intervention, of the plurality of healthcare interventions, is simulated on the particular subject from the set of simulated subjects.

18. The non-transitory computer-readable storage medium as recited in claim 16, wherein the net cost function represents net cost effects obtained when a particular intervention, of the plurality of healthcare interventions, is simulated on the particular subject from the set of simulated subjects.

19. The non-transitory computer-readable storage medium as recited in claim 16, comprising instructions which, when executed, cause:

for a particular intervention, of the plurality of healthcare interventions, and the particular subject, of the set of simulated subjects, having associated initial values:

applying the benefit function to the associated initial values and generating a predicted benefit value that is obtainable by simulating the particular intervention on the particular subject;

applying the net cost function to the associated initial values and generating a predicted net cost value that is obtainable by simulating the particular intervention on the particular subject;

storing the predicted benefit value and the predicted net cost value for the particular intervention.

20. The non-transitory computer-readable storage medium as recited in claim 19, comprising instructions which, when executed, cause applying one or more regression methods when generating the predicted benefit value and generating the predicted net cost value, wherein the one or more regression methods are selected from: generalized linear and non-linear regressions, logistic and Poisson regressions, supervised machine learning algorithms, neural networks, support vector machines, response surface modeling, and multivariate adaptive regression splines.

* * * * *